(12) United States Patent
King et al.

(10) Patent No.: US 8,434,626 B2
(45) Date of Patent: May 7, 2013

(54) SYSTEM AND RELATED METHOD FOR CONCENTRATING BIOLOGICAL CULTURE AND CIRCULATING BIOLOGICAL CULTURE AND PROCESS FLUID

(75) Inventors: John D. H. King, Santa Monica, CA (US); Keeney D. Willis, Palo Alto, CA (US)

(73) Assignee: Combined Power, LLC, Santee, CA (US)

( * ) Notice: Subject to any disclaimer, the term of this patent is extended or adjusted under 35 U.S.C. 154(b) by 390 days.

(21) Appl. No.: 12/705,902

(22) Filed: Feb. 15, 2010

(65) Prior Publication Data

US 2010/0210003 A1    Aug. 19, 2010

Related U.S. Application Data

(60) Provisional application No. 61/152,949, filed on Feb. 16, 2009.

(51) Int. Cl.
*B03B 5/00* (2006.01)

(52) U.S. Cl.
USPC ............... 209/501; 209/725; 435/289.1

(58) Field of Classification Search ......... 209/459, 209/500, 501, 725; 210/194; 435/257.1, 435/289.1
See application file for complete search history.

(56) References Cited

U.S. PATENT DOCUMENTS

| | | | | |
|---|---|---|---|---|
| 1,611,478 A * | 12/1926 | Massey | | 406/156 |
| 3,378,018 A * | 4/1968 | Lawter | | 134/109 |
| 4,545,909 A * | 10/1985 | Atkinson et al. | | 210/618 |
| 4,589,927 A * | 5/1986 | Allen et al. | | 134/25.1 |
| 4,681,685 A * | 7/1987 | Sutton et al. | | 210/618 |
| 4,892,818 A * | 1/1990 | Ramp | | 435/30 |
| 4,900,445 A * | 2/1990 | Flanigan et al. | | 210/512.1 |
| 5,192,441 A | 3/1993 | Sibony et al. | | |
| 5,254,253 A | 10/1993 | Behmann | | |
| 5,603,826 A * | 2/1997 | Welch | | 210/195.1 |
| 5,750,028 A | 5/1998 | Frisch | | |
| 5,951,875 A | 9/1999 | Kanel et al. | | |
| 6,000,551 A * | 12/1999 | Kanel et al. | | 209/164 |
| 7,081,361 B2 | 7/2006 | Pearce, III et al. | | |
| 7,387,723 B2 * | 6/2008 | Jordan | | 210/220 |
| 2003/0036191 A1 | 2/2003 | Frisch | | |
| 2005/0239182 A1 | 10/2005 | Berzin | | |
| 2005/0260553 A1 | 11/2005 | Berzin | | |
| 2007/0289206 A1 | 12/2007 | Kertz | | |
| 2008/0096267 A1 | 4/2008 | Howard et al. | | |
| 2008/0299643 A1 | 12/2008 | Howard et al. | | |
| 2009/0011492 A1 | 1/2009 | Berzin | | |
| 2009/0029445 A1 | 1/2009 | Eckelberry et al. | | |
| 2009/0324799 A1 | 12/2009 | Hartman et al. | | |
| 2011/0062080 A1* | 3/2011 | Galgon et al. | | 210/631 |

* cited by examiner

*Primary Examiner* — Joseph C Rodriguez
(74) *Attorney, Agent, or Firm* — Tsircou Law, P.C.

(57) ABSTRACT

A system and related method for concentrating biological culture and circulating biological culture and process fluid is provided. The system includes a continuous flow separator that removes excess fluid from the culture medium, resulting in a "concentrated medium" of fluid. The concentrated medium is then passed along for further processing to capture the biomass. The overflow, i.e., the extracted fluid, from the continuous flow separator is reintroduced into the container in a manner to circulate the culture medium. Thus, energy from the concentration step is utilized to circulate the culture medium, alleviating the need for significant additional structure for circulating the culture medium. In this manner, the system grows and captures biological material in an energy and capital efficient manner.

20 Claims, 11 Drawing Sheets

SYSTEM AND RELATED METHOD FOR CONCENTRATING BIOLOGICAL CULTURE AND CIRCULATING BIOLOGICAL CULTURE AND PROCESS FLUID

CROSS REFERENCE TO RELATED APPLICATION

This application claims priority to U.S. provisional application No. 61/152,949, filed Feb. 16, 2009, which is hereby incorporated by reference for all purposes.

FIELD OF THE INVENTION

The present invention relates generally to circulation and concentration systems for growing biological culture.

BACKGROUND OF THE INVENTION

The production of algal biomass has increasingly been of interest. The potential usage of such material is found across a wide range of applications, including biofuel feedstock production, fertilizer, nutritional supplements, pollution control, and other uses.

For example, various approaches such as "open-air" and "closed-air," have been considered for mass production of algal biomass. The United States Department of Energy conducted a program called the Aquatic Species Program from 1978 to 1996. The engineering efforts of the program were largely focused on large "open-air" racetrack pond designs. The ponds are so-named based on the fact that the culture medium is conveyed in a complete circuit in a continuous fashion. This flow of culture medium is achieved with large continuously turning paddle wheels, which induce a turbulent flow in the medium. The turbulent flow is necessary to mix the culture so that all algae cells receive sunlight. The ponds are similar in appearance to extremely elongated ovals.

"Closed-air" systems generally refer to systems that contain algal biomass production within a controlled environment, limiting exposure to outside air. Examples of such systems include closed photo-bioreactor structures forming a closed container for housing a culture medium for generating algal biomass. Having a controlled environment helps maximize the generation of algal material by limiting exposure to invasive species as well as controlling other environmental factors that promote algal growth. Similar to open-air systems, closed-air systems require the mixing of algal culture to maximize growth. It should be appreciated that industry standard practice for algal culture is to actively mix the culture.

Additionally, large algal culturing operations require large amounts of water to be transferred between culturing areas and processing areas. This incurs expense in terms of both pumping energy costs and pumping infrastructure capital cost.

Another area of similarity with both closed-air and open-air systems is that algal culture is typically dilute and must be extensively processed to extract the economically beneficial components of the algal cells. Because of this dilute nature of algal culture, often times 1 part in 1000 or less, the processing can be can be very expensive in terms of both capital cost and energy usage. In many cases, conventional processing equipment such as centrifuges and flocculation devices can cost more than the value of the algae that can be harvested over the lifetime of the equipment, and further, the energy required to operate the equipment can be greater than the energy embodied in the algae itself. In both of these two cases, the potential benefits of algal culture for biofuels cannot be realized because the energy and economic costs are too great.

It should be appreciated that a need exists to concentrate the algae culture in a cost effective and energy efficient manner prior to processing in order to maximize the potential benefits of algal culture. The present invention fulfills this need and others.

SUMMARY OF THE INVENTION

In general terms, the present invention provides a system for concentrating biological culture and circulating biological culture and process fluid is provided. The system includes a continuous flow separator that removes excess fluid from the culture medium, resulting in a "concentrated medium" of fluid. The concentrated medium is then passed along for further processing to capture the biomass. The overflow, i.e., the extracted fluid, from the continuous flow separator is reintroduced into the container in a manner to circulate the culture medium. Thus, energy from the concentration step is utilized to circulate the culture medium, alleviating the need for significant additional structure for circulating the culture medium. In this manner, the system grows and captures biological material in an energy and capital efficient manner.

More specifically, by example and not limitation, a system for concentrating biological culture and circulating biological culture and process fluid is provided. The system includes a container housing a culture medium of fluid and biomass and a pump in fluid communication with the culture medium of the container for extracting culture medium from the container. A continuous flow separator is included, having an inlet in fluid communication with the pump for receive culture medium. The continuous flow separator is configured to extract fluid from the culture medium resulting in a concentrate medium and extracted fluid. The concentrated medium exits the continuous flow separator through a first outlet. The extracted fluid exits continuous flow separator through a second outlet. An eductor pump having a motive connection is coupled to the second outlet of the continuous flow separator. The eductor pump further includes a suction connection coupled to a pipe that provides a fluid at a velocity lower than the velocity of the extracted fluid at the motive connection. The eductor pump is mounted in fluid communication to the container to aid in circulating the culture medium within the container.

A method system for concentrating biological culture and circulating biological culture and process fluid is also provided. In an exemplary embodiment in accordance with the invention, the method can include the following steps:

providing a closed bioreactor housing a culture medium of fluid and biomass, the closed bioreactor having a inlet bulkhead and a outlet bulkhead;

pumping the culture medium from the outlet bulkhead of the container to a continuous flow separator in a continuous manner via a pump in fluid communication with the container and the continuous flow separator;

extracting fluid from the culture medium received by the continuous flow separator through an inlet in fluid communication with the pump for receiving culture medium, resulting in a concentrated medium and an extracted fluid;

providing the concentrated medium for secondary processing for removal of biomass in a continuous manner, in which the concentrated medium exits the continuous flow separator through a first outlet;

providing the extracted fluid from the continuous flow separator to a motive connection of an eductor pump, the eductor pump further includes a suction connection coupled to a pipe that provides a fluid at a velocity lower than the velocity of the extracted fluid at the motive connection; and circulating the culture medium in the container by injecting effluent from the eductor pump into the container.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION OF EXEMPLARY EMBODIMENTS

Figure 1:
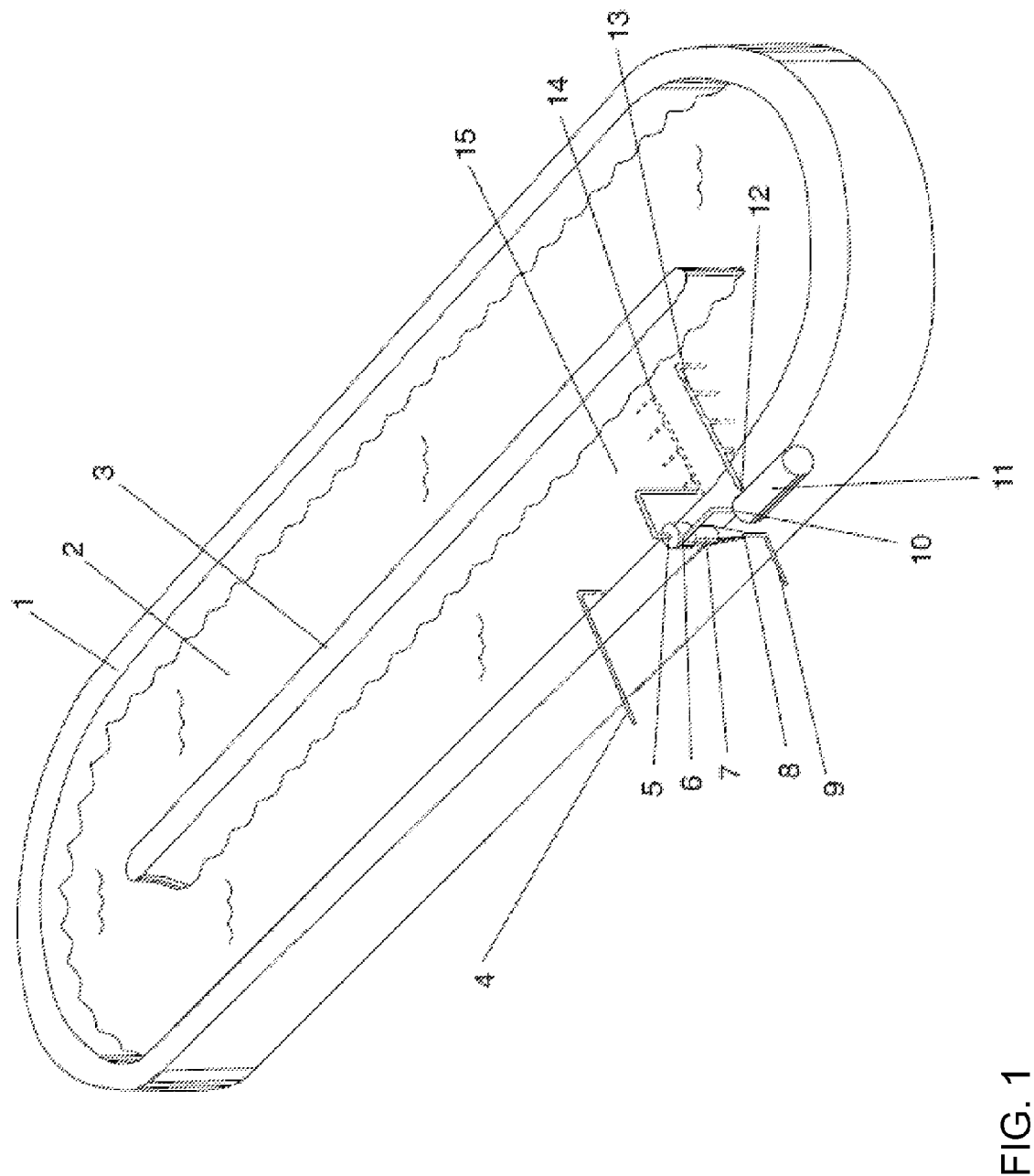
FIG. 1 is a perspective view of a first embodiment of a system for growing algal biomass in accordance with the present invention.
Figure 2:
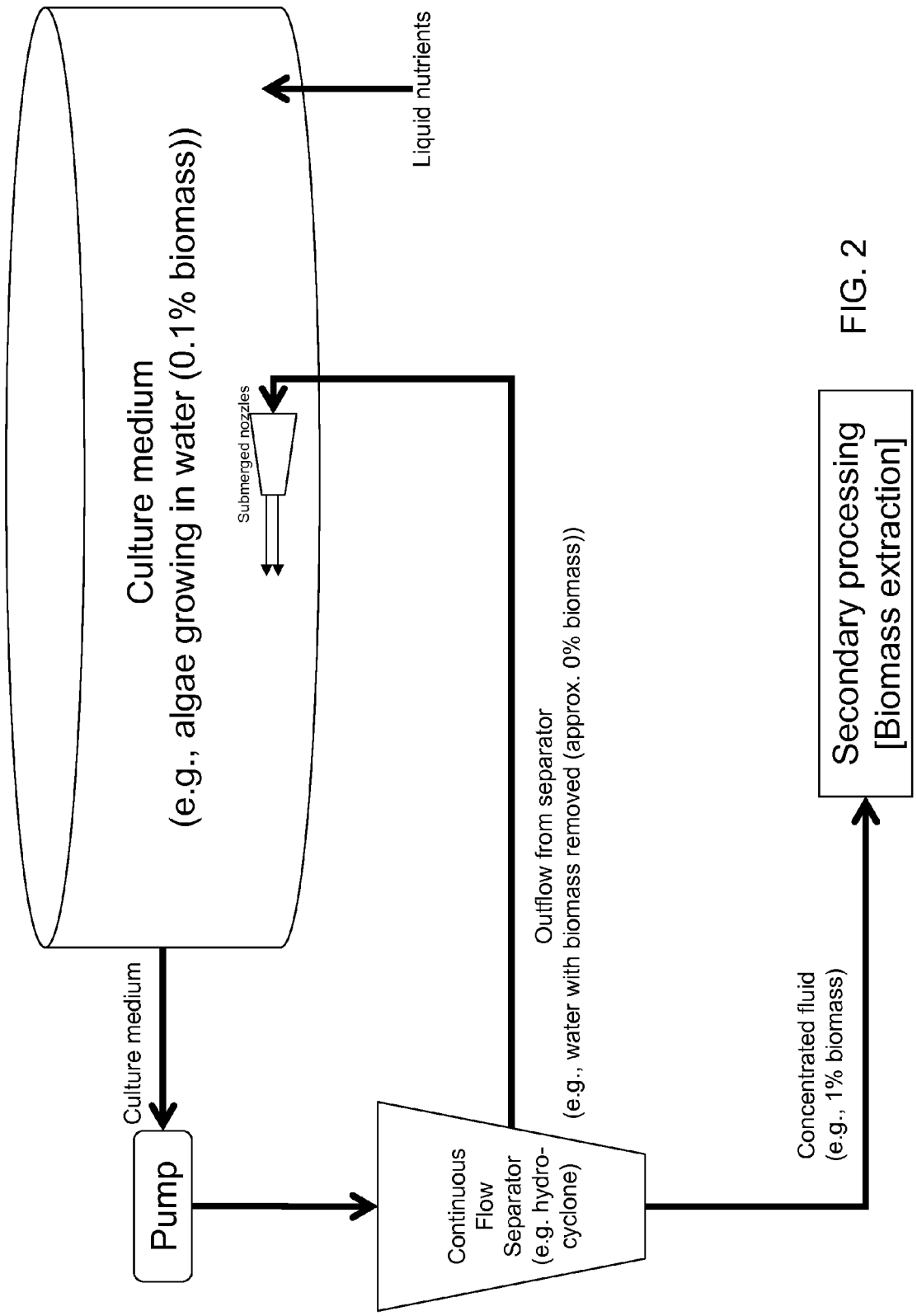
FIG. 2 is a simplified flow diagram for the system of FIG. 1.

With reference now to the drawings, and particularly FIGS. 1 and 2, there is shown a system having a container 1 housing a culture medium 2. The container is configured as an open-air, racetrack pond 1 having a center divider 3. The culture medium travels around the pond generally clockwise. The system includes a pipe 4 that adds water and nutrients to the culture medium to maintain fluid levels of the culture medium and to facilitate algal growth.

To extract algae from the culture medium, the system concentrates the ratio of algae to fluid, by passing the culture medium through a continuous flow separator to remove excess water, resulting in a "concentrated medium" of fluid. The concentrated medium is then passed along for further processing to remove the algae. The outflow, i.e., the extracted water, from the continuous flow separator is reintroduced into the container in a manner to circulate the culture medium. Thus, energy from the concentration step utilized to circulate the culture medium, alleviating the need for significant additional structure for circulating the culture medium. In this manner, the system grows and captures biological material in an energy and capital efficient manner.

More particularly, the system includes a pump 11 that provides culture medium 3 to a continuous flow separator. In this embodiment, a hydrocyclone 7 is used. The pump inlet 12 is coupled via piping to multiple submerged inlets 13 in the culture medium 2 within the pond 1. The outlet 10 of the pump provides the culture medium to the inlet 6 of the hydrocyclone 7 at high pressure.

The hydrocyclone 7 processes the culture medium removing water from the medium, resulting in a "concentrated fluid" having a higher ratio of biomass to liquid than that of the culture medium. The output 8 of the hydrocyclone (a.k.a., underflow outlet) provides the concentrated fluid for secondary processing, in which the biomass is further extracted from the fluid.

The fluid extracted from the culture medium ("the extracted water") exits the hydrocyclone via overflow outlet 5. The extracted water exits the hydrocyclone at relatively high pressure. The extracted water travels through piping to high-velocity jets 14 submerged in the culture medium within the pond 1. In the exemplary embodiments, several jets are used. The jets are oriented to facilitate clockwise flow of the culture medium 2 within the pond 1. The flow within the culture medium includes a transition area 15 in which the high-velocity jets impart momentum to the relatively low velocity culture medium 2. In this manner, the culture medium is circulated to ensure algae of the culture medium is exposed to sunlight to promote algal growth.

Figure 3:
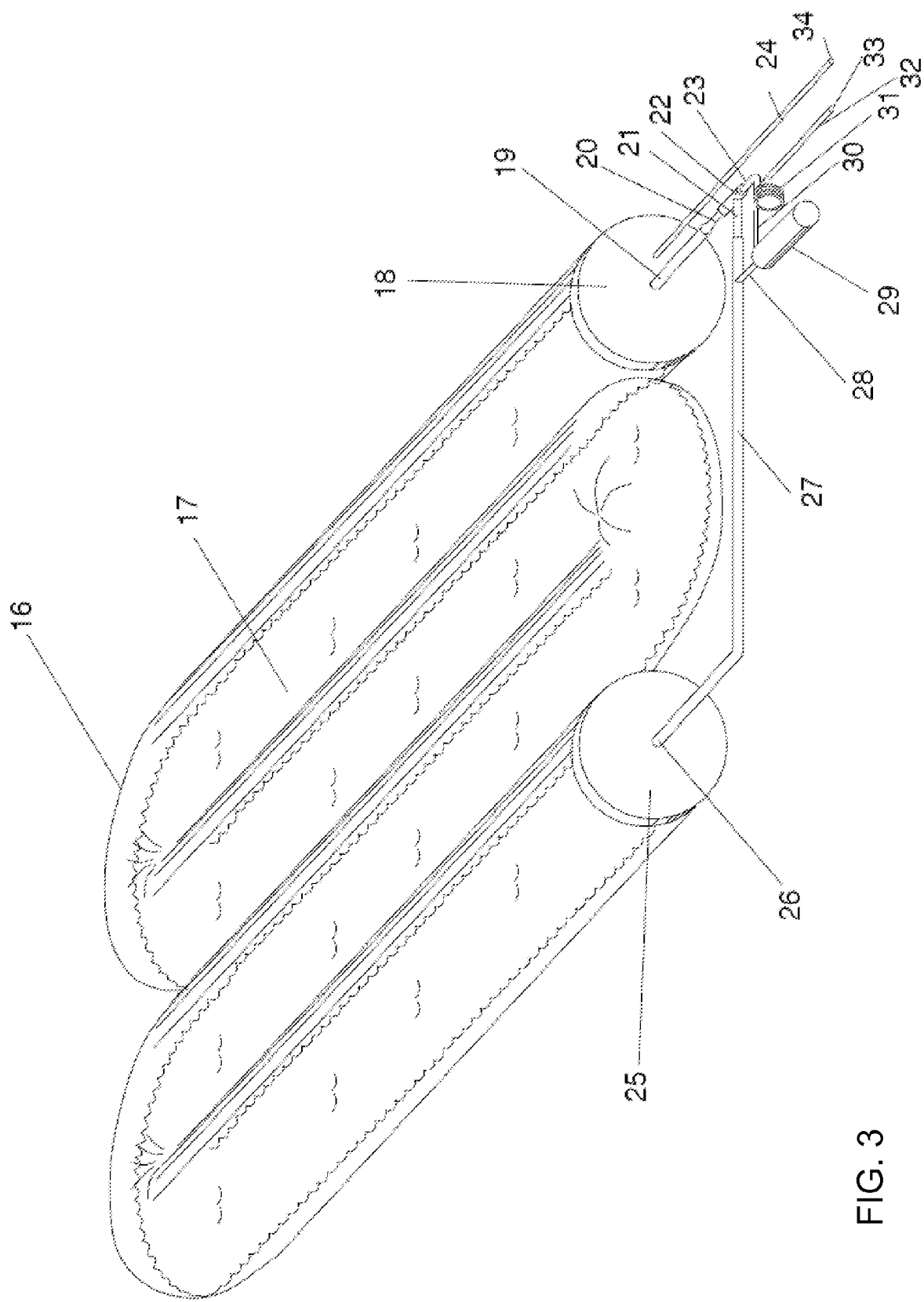
FIG. 3 is a perspective view of a second embodiment of a system for growing algal biomass in accordance with the present invention.
Figure 4:
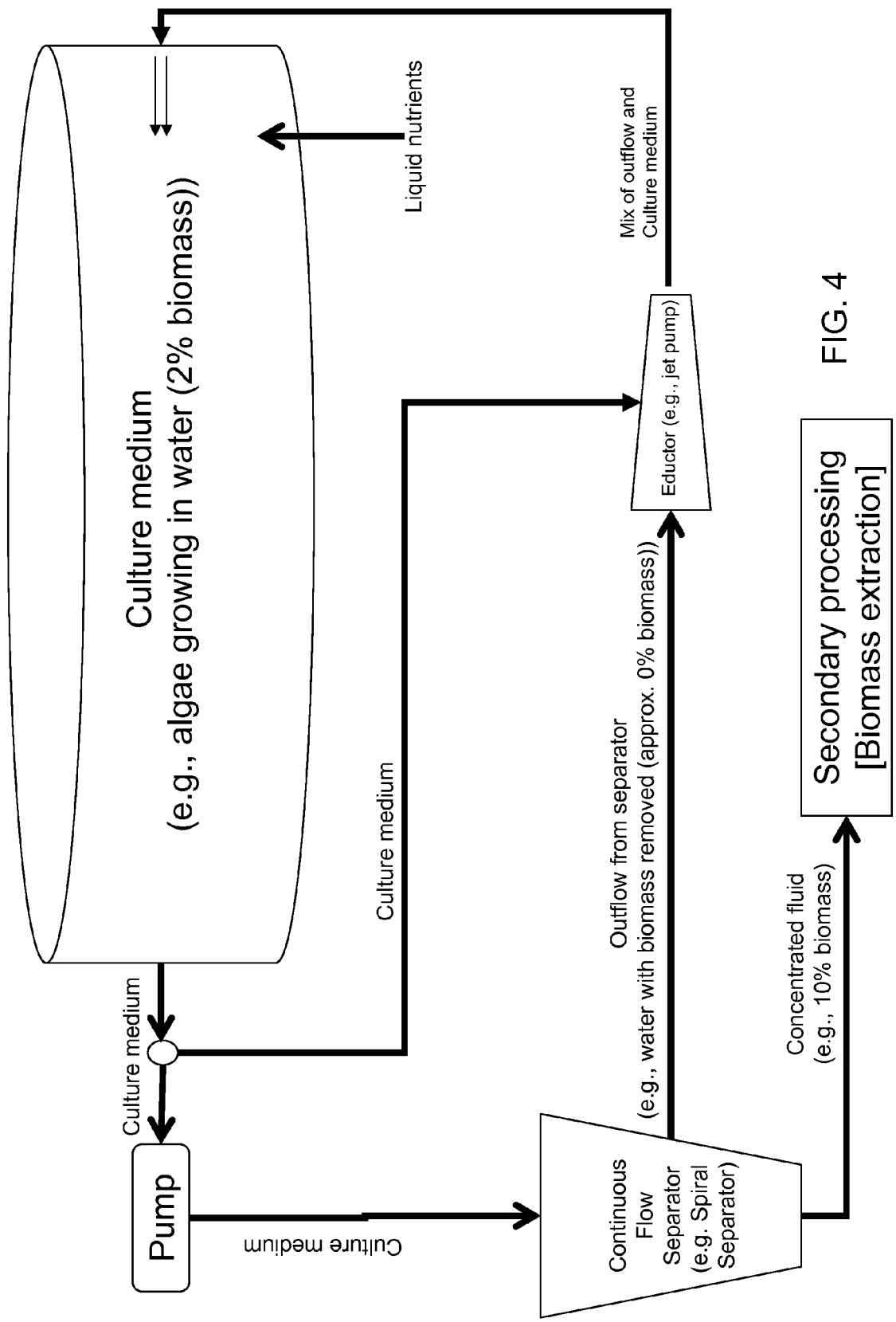
FIG. 4 is a simplified flow diagram for the system of FIG. 3.

With reference now to FIGS. 3 and 4, a second embodiment is shown, depicting a system having a container, a closed-air bioreactor 16, housing a culture medium 17. The system includes bulkheads 18, 25 disposed on opposing ends of the bioreactor. The system is configured to cause the culture medium to flow from the inlet bulkhead 18 to the outlet bulkhead 25. More particularly, the system includes a pump 29 that provides culture medium 17 from an outlet 26 of the bulkhead 25 to a continuous flow, curved-channel separator 30 (spiral separator) via a return pipe 27.

An inlet to the pump 29 is in fluid communication with the return pipe 27 via a suction fitting 28. The pump draws a measure of culture medium from the return pipe, providing it to the spiral separator. More particularly, an outlet 30 from the pump provides culture medium at high pressure to the spiral separator 30. The spiral separator removes excess water, providing concentrated fluid 32 for secondary processing to extract the biomass. The excess water leaves the spiral separator at a relatively high velocity.

The excess water returns to the bioreactor 16 via a pipe 23 that feeds into a motive connector of an eductor pump 22. The eductor further includes a suction inlet 21 connected to the return pipe 27. The eductor combines the culture medium from the return pipe 27 with the excess water from the pipe 23, discharging the combination into the bioreactor 16 at the bioreactor inlet 19. The eductor ensures that the combined fluid enters the bioreactor at a desirable velocity to facilitate effective circulation of the culture medium.

In the present embodiment, the system further includes a pipe 4 that adds water and nutrients to the culture medium to maintain fluid levels of the culture medium and to facilitate algal growth.

Figure 5:
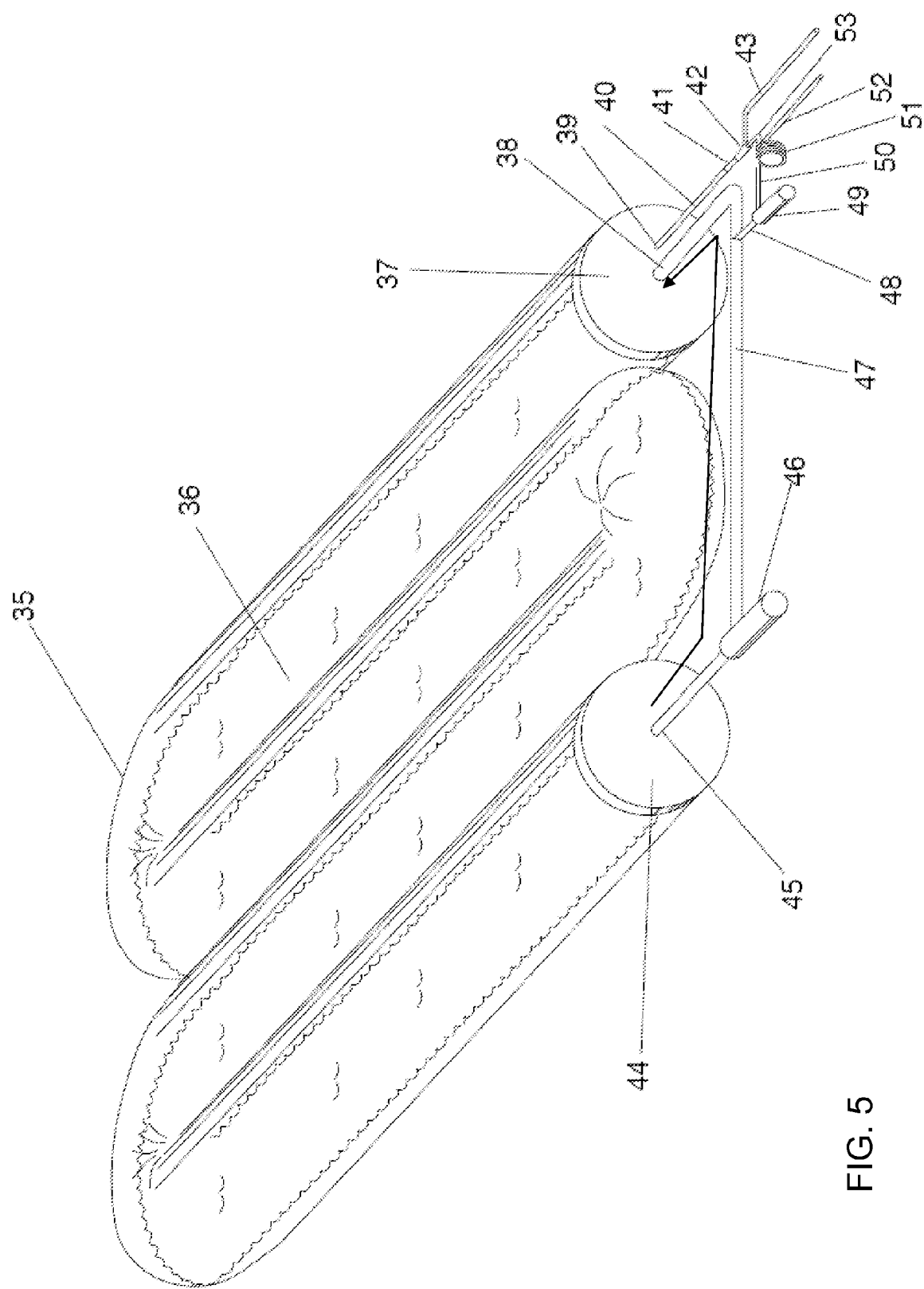
FIG. 5 is a perspective view of a third embodiment of a system for growing algal biomass in accordance with the present invention.
Figure 6:
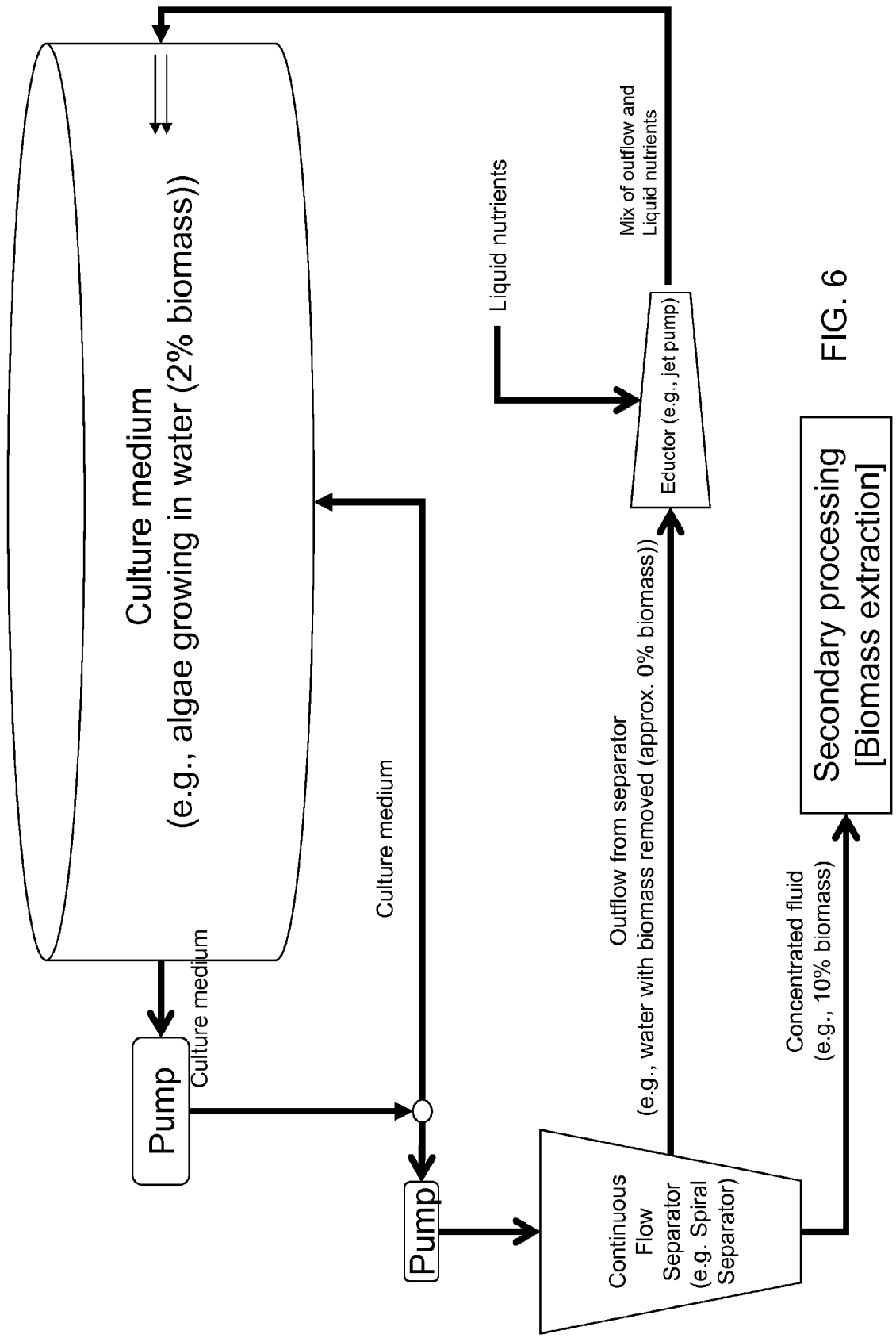
FIG. 6 is a simplified flow diagram for the system of FIG. 5.

With reference now to FIGS. 5 and 6, a third embodiment is shown, depicting a system having a closed-air bioreactor 35 housing a culture medium 36. The system includes bulkheads 37, 44 disposed on opposing ends of the bioreactor. The system is configured to cause the culture medium to flow from the inlet bulkhead 37 to the outlet bulkhead 44.

In this embodiment, the system includes an inline pump 46 that provides culture medium 36 from an outlet 45 of the bulkhead 44 to a return pipe 47. A second pump 49 includes an inlet operatively coupled to a suction fitting 48 on the return pipe 47. Outlet from the second pump 49 provides culture medium to a continuous flow, curved-channel separator 51 (spiral separator). High-velocity excess water 53 from the spiral separator feeds to a motive connector of an eductor 41. The system further includes a pipe 43 that feeds nutrient fluid to the suction connection 42 of the eductor. The combined fluid exits the eductor at a velocity desirable for circulating the culture medium 36 within the bioreactor.

The return pipe 47 is coupled to the inlet bulkhead 37 at inlet 38. The culture medium entering the bioreactor 35 from the return pipe can contribute to the flow of the culture medium 36 within the bioreactor. In related embodiments, the return pipe can extend into the bioreactor a prescribed distance, so that the end is submerged in the culture medium. The system can further include a submerged jet pump couple to the end of the return pipe to further facilitate circulation of the culture medium.

Figure 7:
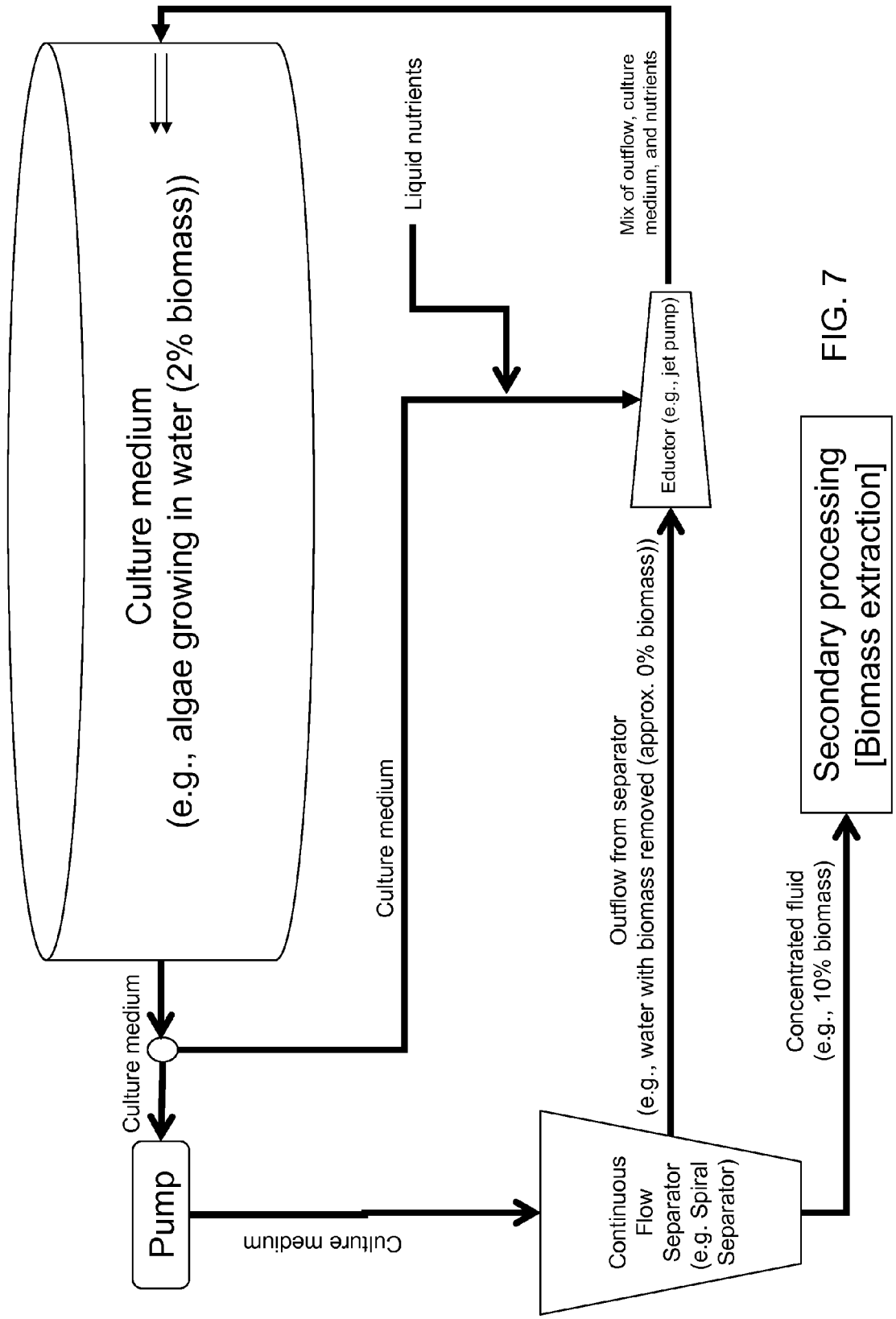
FIG. 7 is a simplified flow diagram for of a fourth embodiment of a system for growing algal biomass in accordance with the present invention.

With reference now to FIG. 7, a fourth embodiment is shown. The system is generally similar to the embodiment depicted in FIGS. 4 and 5. However, in this embodiment, the liquid nutrients and the culture medium in the return pipe are combined and sent to the suction connection of the eductor.

Figure 8:
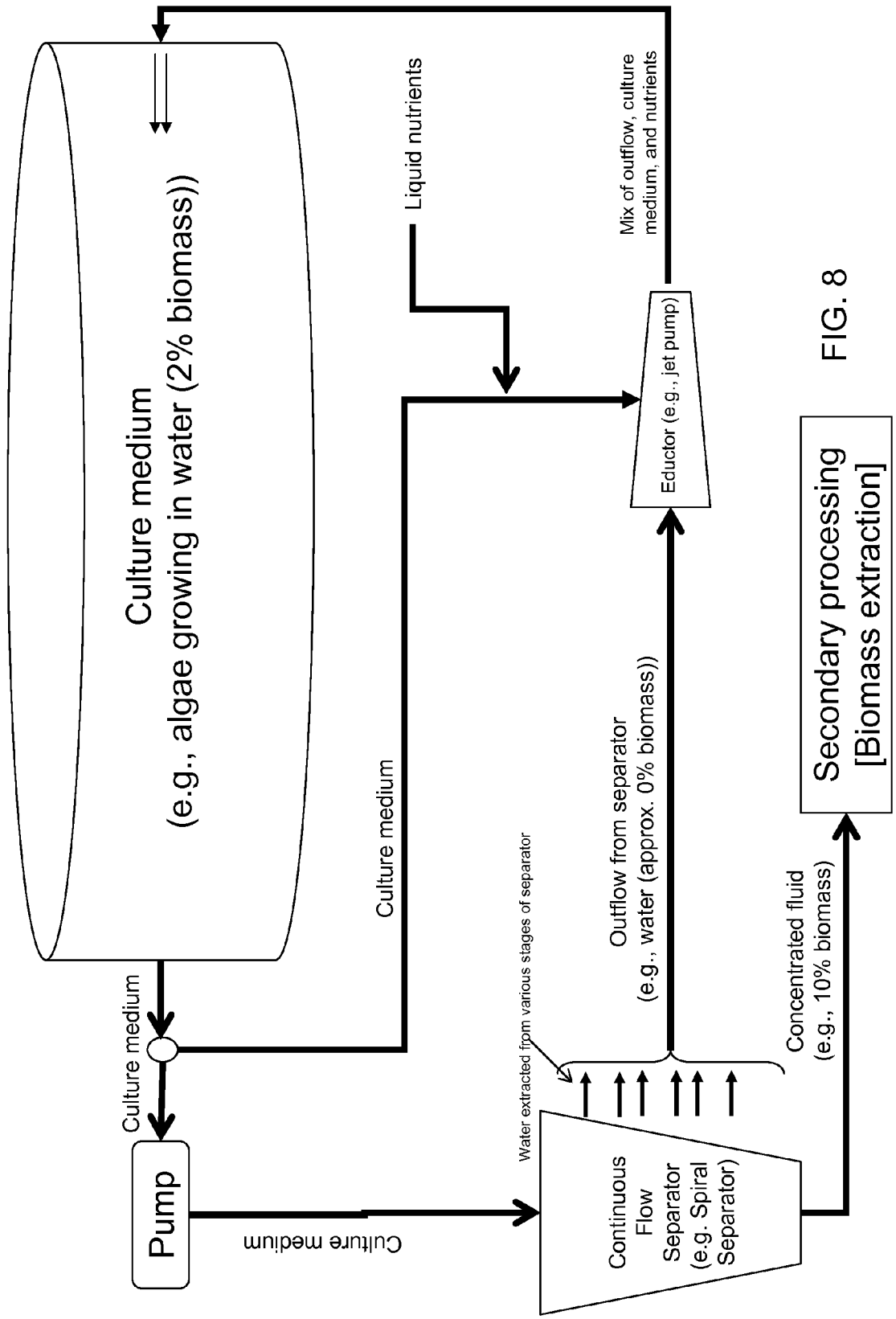
FIG. 8 is a flow diagram including a spiral separator.

Referring now to FIG. 8, the system includes a spiral separator that is configured to remove excess water at a plurality of the locations along its length. The excess water removed early along the length of the spiral separator will have substantial momentum, since it has not been exposed to excessive friction within the spiral separator. Thus, the net effect of this configuration provides an outflow of excess water having higher net energy than spiral separators the require all excess water to travel the entire length of the spiral separator. Spiral separators having multiple extraction locations for excess water can be in various other embodiment of the invention, including those discussed above.

Figure 9:
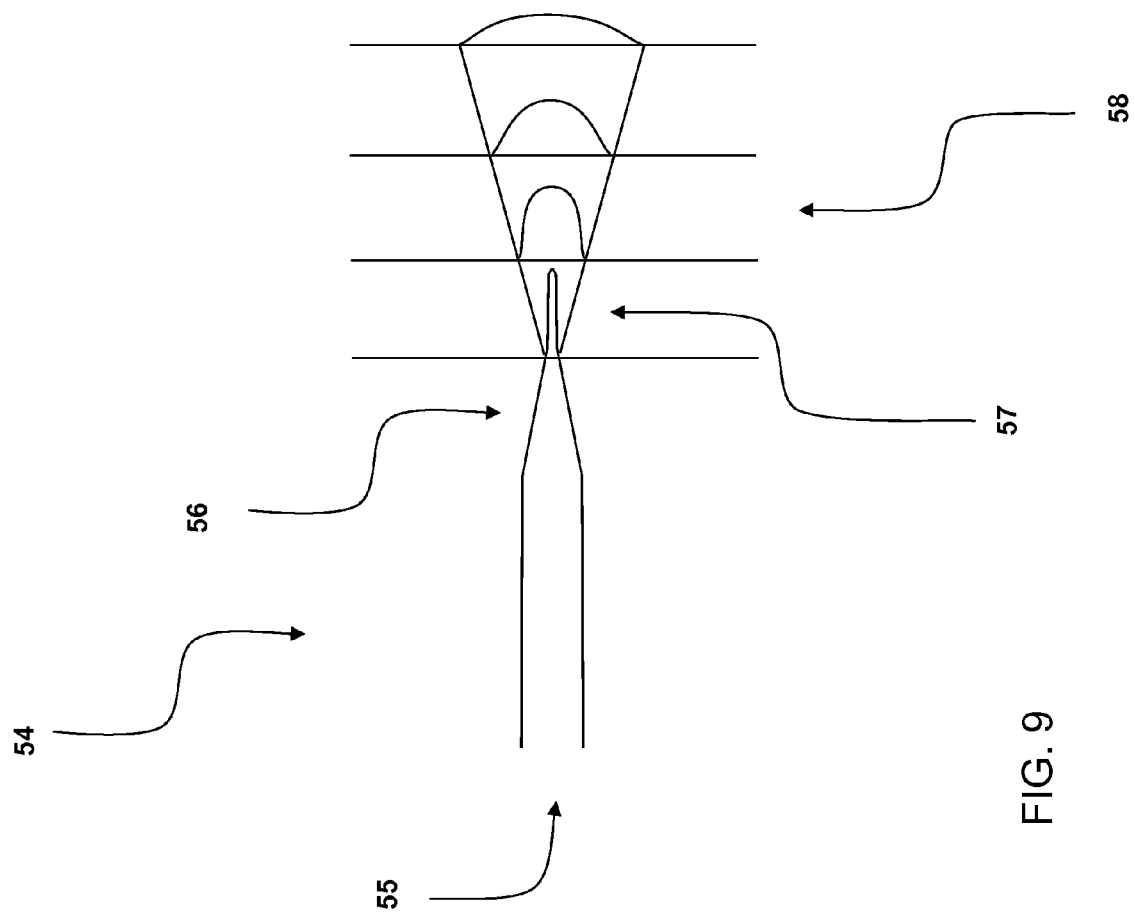
FIG. 9 is a simplified view depicting a single outlet port submerged in a container of culture medium in accordance with the invention, the outlet port receives excess fluid from a continuous flow separator (not shown).

With reference now to FIG. 9, a single outlet port 54 is shown submerged in a container of culture medium in accordance with the invention. The outlet port receives excess fluid 55 from a continuous flow separator (not shown). Fluid 55 exits the continuous flow separator with some internal pressure. The energy contained in the fluid as pressure per unit volume is converted to kinetic energy within the nozzle 56. Some energy is lost within the nozzle because the nozzle will have some efficiency factor below 100%. The kinetic energy imparted at the nozzle causes a high velocity, low-pressure jet to exit the nozzle 57. An entrainment zone 58 is created within which momentum from the fast moving jet is transferred to the slower moving fluid. The velocity profile of the entrainment zone is shown in four successive steps 58. Some energy is lost in the entrainment zone 58 because the momentum transfer efficiency factor will always be less than 100%. The speed of the jet slows down as it entrains more and more of the surrounding slow moving fluid. In this way, energy is transferred from the high velocity, low-volume flow rate jet to the low velocity, high-volume flow-rate body of fluid.

Figure 10:
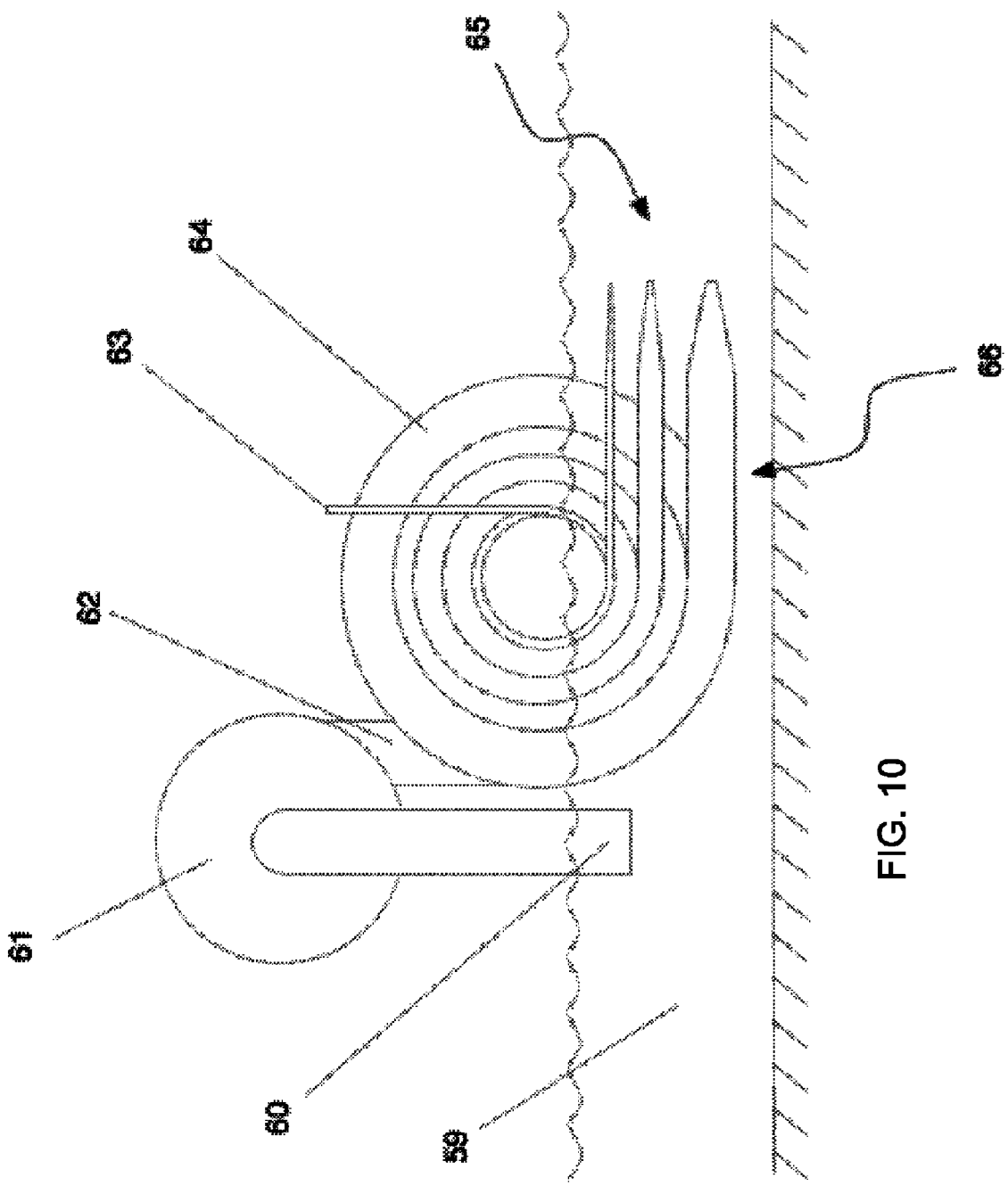
FIG. 10 is a simplified view depicting multiple exit nozzles submerged in a container of culture medium in accordance with the invention.

With reference now to FIG. 10, an embodiment of this invention is shown with multiple exit nozzles positioned with algae culture 59. An inlet is shown 60, which takes in a low volume of culture to be filtered. A pump 61 draws in culture. The culture exits at 62, with high pressure and enters the continuous flow separator, 64. Within the separator, algae cells are separated out, and purified culture medium exits at multiple outlets, 66 with various levels of residual internal pressure. The residual pressure at each outlet is converted to kinetic energy at the nozzles, 65, and exits into the body of culture, imparting kinetic energy and circulating the fluid volume. The separated algae cells leave at the final outlet 63, which is concentrated algal culture, to be sent to central processing facility away from the algae growth system.

In selected embodiments in accordance with the invention, certain design considerations can be taken into account, particularly for a system using a closed photobioreactor that is substantially filled with liquid culture media, to include the following:

t=time
$C_t$=the concentration of algae at time t
$C_0$=initial concentration
m=growth rate constant that is dependent on species and culture conditions
$V_c$=culture volume
$N_t$=number of cells in culture at time t
H=total number of cells harvested by a continuous flow separator
$E_s$=separator efficiency
$Q_s$=separator volume flow rate
Re=Reynolds number
ρ=fluid density
v=fluid velocity
A=cross-sectional area of culture conduit
D=characteristic diameter of the conduit
   D=pipe diameter in circular pipes
   D=4A/P where P is the wetted perimeter
μ=kinematic viscosity of fluid
f=friction factor
L=length of the conduit
e=absolute roughness of the surface of the conduit
$Q_O$=volume flow rate out of continuous flow separator at outlet O
$P_O$=internal pressure of continuous flow separator at outlet O
$\epsilon_{nO}$=Efficiency factor of nozzle O, converting pressure head into kinetic energy
$\epsilon_{mO}$=Efficiency factor at jet O, in converting kinetic energy from fast moving, low volume jet to slow moving, large volume slug of water.

Figure 11:
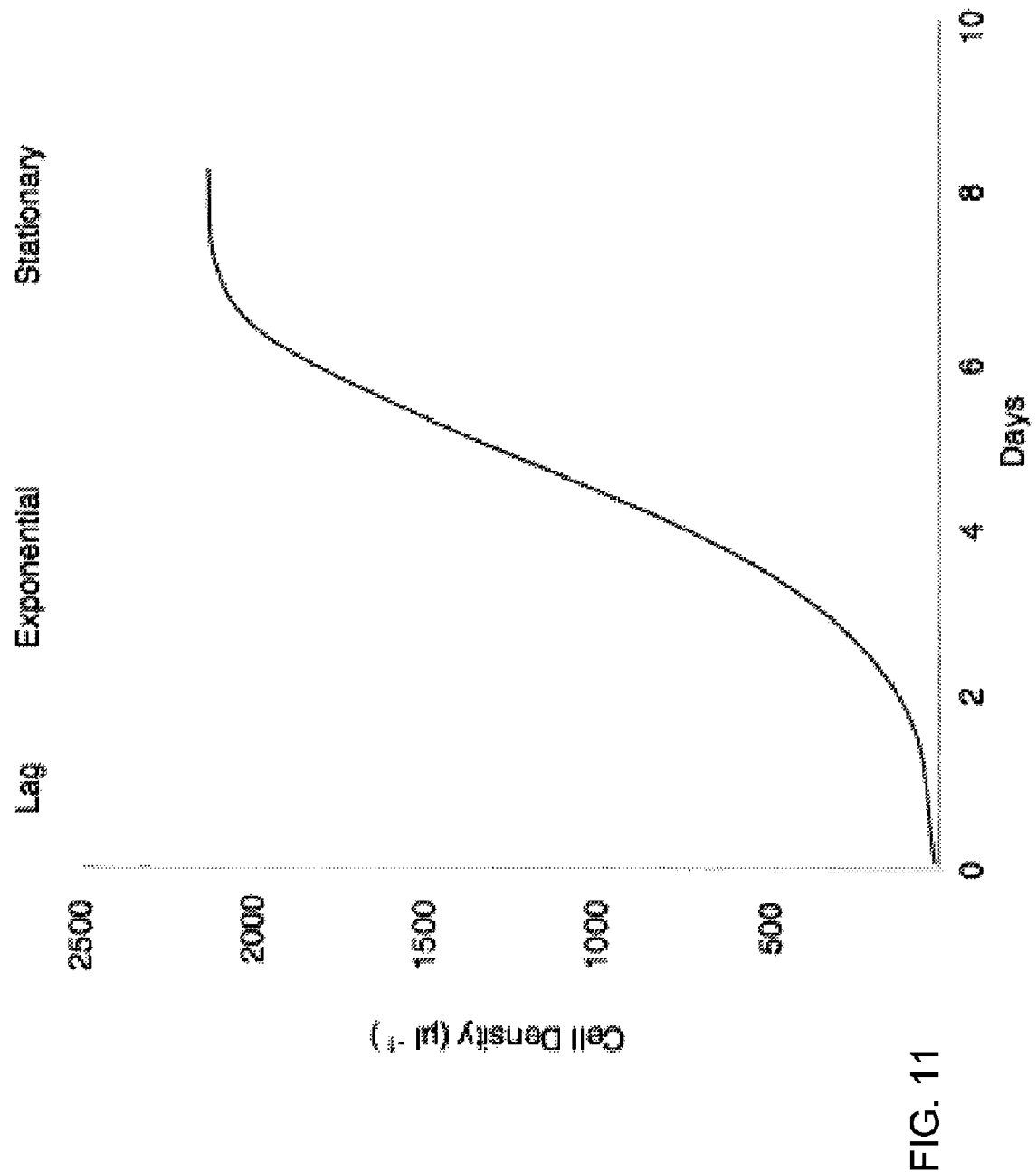
FIG. 11 is a graph depicting an exemplary algal growth curve.

Algae growth kinetics define a typical growth curve as shown in FIG. 11. During the exponential phase, algal concentration is described by:

$$C_t = C_0 e^{mt}$$

The total number of algae cells present in culture, $N_t$, at any given time, t, is given by:

$$N_t = C_t V_c$$

Holding the culture volume as constant, the total change in algal cells in a given time period, ΔN, is then:

$$\Delta N = N_2 - N_1$$

For continuous flow separators, the number of algal cells harvested, H, is defined as:

$$H = C_r E_s Q_s \Delta t$$

To maximize algal biomass production, culture must be grown until near the end of the exponential phase is reached and then harvested at a rate to keep the concentration at the same level to avoid going into the stationary phase.

The harvest rate must equal the growth rate at the desired equilibrium point. That is:

$$H = \Delta N \qquad \text{Equation 1}$$

Most algae growth systems require circulation. The reason for circulation is to keep the algae from settling out of culture, to ensure that all algae receive adequate illumination, and to keep nutrients well mixed throughout the culture. Mixing is achieved in algal mass culture through turbulent mixing, both in raceway ponds and closed photobioreactors. To achieve turbulent flow conditions, the Reynolds number Re must be greater than or equal to 3000.

$$Re = \rho v D / \mu$$

$$Re > 3000$$

$$v > 3000 \, \mu / \rho D$$

The pressure head, p, required to maintain the minimum velocity is:

$$p = \frac{f L \rho v^2}{D2}$$

The friction factor is found iteratively using a standard Moory chart. An experimentally determined curve fit is given by Colebrook (Colebrook, C. F. (1938), "Turbulent Flow in Pipes", Journal of the Inst. Civil Eng. (11), p 133):

$$\frac{1}{\sqrt{f}} = -2 \log\left(\frac{e/D}{Re\sqrt{f}} + \frac{2.51}{3.7}\right)$$

The power input, $P_{in}$, required to maintain this flow is simply the pressure head times the volume flow rate:

$$P_{in} = p v A$$

The recoverable power for a continuous flow separator is given by:

$$P_{r_O} = \sum Q_O P_O \varepsilon_{nO} \varepsilon_{mO}$$

To drive circulation in an algal growth system using the recoverable energy from a continuous flow separator, the following design constraint is imposed:

$$P_{in} = P_r \qquad \text{Equation 2a}$$

Equation 1 and Equation 2a provide design guidelines for a specific configuration of algal growth system, alga species, and growth conditions.

Of course, if desired, only some of the energy from the harvesting device can be used to drive circulation of culture and the rest diverted for other purposes. Some or all of the recoverable power from the continuous flow separator can be diverted to drive other flow, such as the flow in the make up water necessary for nutrient replenishment in algal growth systems. In this case, the following holds:

$$P_{in} < P_r \qquad \text{Equation 2b}$$

Further, if a system is designed such that only part of the pressure head necessary to drive culture circulation and mixing is supplied by recoverable power using this invention, then a separate, complementary circulation system would be necessary. In such a case, the following holds:

$$P_{in} > P_r \qquad \text{Equation 2c}$$

Naturally, the greatest cost, energy, and complexity benefits are possible when Equation 2a holds.

It should be appreciated that for algae culture mixing and circulation, the desired flow parameters are low pressure, low velocity, and high volume flow rate. For a continuous flow separator with high separation efficiency, the desired parameters are typically, high pressure, high velocity and low volume flow rate. These two contradictory flow regimes would typically call for two different pumping systems, but by coupling them with entrainment pumping as described by this invention, only one pumping system is needed, thereby lowering capital cost, energy usage, and system complexity among other advantages.

Although the invention has been disclosed in detail with reference only to the exemplary embodiments, those skilled in the art will appreciate that various other embodiments can be provided without departing from the scope of the invention. Accordingly, the invention is defined only by the claims set forth below.

What is claimed is:

1. A system for concentrating biological culture and circulating biological culture and process fluid, comprising:
   a container housing a culture medium of fluid and biomass;
   a pump having an outlet and an inlet configured to extract culture medium from the container; and
   a continuous flow separator having an inlet in fluid communication with the outlet the pump for receiving culture medium from the pump, the continuous flow separator configured to extract fluid from the culture medium resulting in a concentrated medium and extracted fluid, the concentrated medium exits the continuous flow separator through a first outlet, and the extracted fluid exits continuous flow separator through a second outlet;
   wherein the extracted fluid is directed for reintroduction into the container to facilitate circulation of the culture medium within the container;
   wherein the concentrated medium is directed for secondary processing for removal of biomass.

2. A system as defined in claim 1, wherein the continuous flow separator comprises a hydrocyclone.

3. A system as defined in claim 1, wherein the continuous flow separator comprises a curved, closed-channel, laminar flow, particle separator.

4. A system as defined in claim 1, wherein the container is an open air pond.

5. A system as defined in claim 1, wherein the container is a closed bioreactor.

6. A system as defined in claim 1, further comprising a plurality of pump jets in fluid communication with the second outlet of the continuous flow separator, the plurality of pump jets are submerged in the culture medium of the container such that they facilitate circulation of the culture medium within the container.

7. A system for concentrating biological culture and circulating biological culture and process fluid, comprising:
   a container housing a culture medium of fluid and biomass;
   a pump having an outlet and an inlet configured to extract culture medium from the container;
   a continuous flow separator having an inlet in fluid communication with the outlet of the pump for receive culture medium, the continuous flow separator configured to extract fluid from the culture medium resulting in a concentrated medium and extracted fluid, the concentrated medium exits the continuous flow separator through a first outlet, the extracted fluid exits continuous flow separator through a second outlet; and an eductor pump having a motive connection coupled to the second outlet of the continuous flow separator, the eductor pump further includes a suction connection coupled to a pipe that provides a fluid at a velocity lower than the velocity of the extracted fluid at the motive connection, the eductor pump mounted in fluid communication to the container to aid in circulating the culture medium within the container.

8. A system as defined in claim 7, wherein the fluid provided through the suction connection of the eductor pump is a nutrient medium used to feed biological culture.

9. A system as defined in claim 7, wherein the continuous flow separator comprises a hydrocyclone.

10. A system as defined in claim 7, wherein the continuous flow separator comprises a curved, closed-channel, laminar flow, particle separator.

11. A system as defined in claim 7, wherein the container is an open air pond.

12. A system as defined in claim 7, further comprising a plurality of pump jets in fluid communication with the second outlet of the continuous flow separator, the plurality of pump jets are submerged in the culture medium of the container such that they facilitate circulation of the culture medium within the container.

13. A system as defined in claim 7, a closed bioreactor housing a culture medium of fluid and biomass, the closed bioreactor having an inlet bulkhead and an outlet bulkhead.

14. A system as defined in claim 13, wherein the fluid provided through the suction connection of the eductor pump is a nutrient medium used to feed biological culture.

15. A system as defined in claim 13, wherein the continuous flow separator comprises a hydrocyclone.

16. A system as defined in claim 13, wherein the continuous flow separator comprises a curved, closed-channel, laminar flow, particle separator.

17. A method for concentrating biological culture and circulating biological culture and process fluid, comprising:
 providing a closed bioreactor housing a culture medium of fluid and biomass, the closed bioreactor having an inlet bulkhead and an outlet bulkhead;
 pumping the culture medium from the outlet bulkhead of the container to a continuous flow separator in a continuous manner via a pump in fluid communication with the container and the continuous flow separator;
 extracting fluid from the culture medium received by the continuous flow separator through an inlet in fluid communication with the pump for receiving culture medium, resulting in a concentrated medium and an extracted fluid;
 providing the concentrated medium for secondary processing for removal of biomass in a continuous manner, in which the concentrated medium exits the continuous flow separator through a first outlet;
 providing the extracted fluid from the continuous flow separator to a motive connection of an eductor pump, the eductor pump further includes a suction connection coupled to a pipe that provides a fluid at a velocity lower than the velocity of the extracted fluid at the motive connection; and
 circulating the culture medium in the container by injecting effluent from the eductor pump into the container.

18. A method as defined in claim 17, wherein the fluid provided through the suction connection of the eductor pump is a nutrient medium used to feed biological culture.

19. A method as defined in claim 17, wherein the continuous flow separator comprises a hydrocyclone.

20. A method as defined in claim 17, wherein the continuous flow separator comprises a curved, closed-channel, laminar flow, particle separator.

* * * * *